(12) United States Patent
Bhawalkar et al.

(10) Patent No.: US 10,925,669 B2
(45) Date of Patent: Feb. 23, 2021

(54) SMOKE EVACUATION SYSTEM

(71) Applicant: Candela Corporation, Wayland, MA (US)

(72) Inventors: Jayant Bhawalkar, Auburndale, MA (US); Amit Paranjape, Acton, MA (US); Kevin Schomacker, Maynard, MA (US); Craig Langlois, Clinton, MA (US); Herbert Otterson, Needham, MA (US)

(73) Assignee: Candela Corporation, Wayland, MA (US)

( * ) Notice: Subject to any disclaimer, the term of this patent is extended or adjusted under 35 U.S.C. 154(b) by 0 days.

(21) Appl. No.: 15/487,466

(22) Filed: Apr. 14, 2017

(65) Prior Publication Data

US 2018/0296268 A1 Oct. 18, 2018

(51) Int. Cl.
*A61B 18/20* (2006.01)
*A61M 1/00* (2006.01)
*A61N 5/06* (2006.01)
*B01D 46/00* (2006.01)
*A61B 18/00* (2006.01)

(52) U.S. Cl.
CPC ......... *A61B 18/203* (2013.01); *A61M 1/0035* (2014.02); *A61M 1/0066* (2013.01); *A61N 5/0616* (2013.01); *B01D 46/0047* (2013.01); *A61B 2018/00452* (2013.01); *A61B 2018/00577* (2013.01); *A61B 2018/20351* (2017.05); *A61B 2218/008* (2013.01); *B01D 2279/00* (2013.01)

(58) Field of Classification Search
CPC ..... A61B 18/20; A61B 18/201; A61B 18/203; A61B 18/222; A61B 2018/225; A61B 2018/2253; A61B 2018/00452; A61B 2018/0047; A61B 2018/00476; A61B 2018/00571; A61B 2018/00577; A61B 2018/00625; A61B 2018/00636; A61B 2018/00696; A61B 2018/00708; A61B 2218/00; A61B 2218/001; A61B 2218/007; A61B 2218/008; A61M 1/0023; A61M 1/0031; A61M 1/0035; A61M 1/0037; A61M 1/0039; A61M 1/0043; A61M 1/0056; A61M 1/0066; A61N 5/06; A61N 5/0613; A61N 5/0616; A61N 5/0617; A61N 2005/0626; A61N 2005/0635; A61N 2005/0643; A61N 2005/0644; A61N 2005/067
USPC .......................................... 606/9–11, 13, 15
See application file for complete search history.

(56) References Cited

U.S. PATENT DOCUMENTS 5,336,218 A 12/1994 Linares
5,575,789 A 11/1996 Bell et al.
(Continued)

FOREIGN PATENT DOCUMENTS

WO 1997014364 A1 4/1997
WO 1998004200 A1 2/1998

*Primary Examiner* — Ahmed M Farah
(74) *Attorney, Agent, or Firm* — Manelli Selter PLLC; Edward Stemberger

(57) ABSTRACT

Smoke evacuation system for removal of aerosolized chemical compounds and biological fine particles produced during laser treatment of tissue. The rapid smoke evacuation is achieved by coupling a low capacity vacuum pump to a vacuum valve and a vacuum reservoir to create very high flow rate for very short durations. The opening time of the valve could at least partially overlap the laser pulse duration.

16 Claims, 3 Drawing Sheets

(56) References Cited

U.S. PATENT DOCUMENTS

| | | | |
|---|---|---|---|
| 5,768,740 A | 6/1998 | Bosma et al. | |
| 5,836,909 A * | 11/1998 | Cosmescu | A61B 18/14 |
| | | | 604/35 |
| 5,874,052 A | 2/1999 | Holland | |
| 5,908,403 A | 6/1999 | Krymsky | |
| 5,968,032 A * | 10/1999 | Sleister | A61B 18/00 |
| | | | 604/35 |
| 6,264,649 B1 * | 7/2001 | Whitcroft | A61B 18/203 |
| | | | 604/113 |
| 8,641,488 B1 | 2/2014 | Shvetsov | |
| 2008/0215039 A1 * | 9/2008 | Slatkine | A61B 17/205 |
| | | | 606/9 |
| 2013/0197494 A1 * | 8/2013 | Koifman | A61B 18/203 |
| | | | 606/17 |
| 2014/0276694 A1 * | 9/2014 | Hendrick | A61B 18/245 |
| | | | 606/15 |
| 2016/0193635 A1 | 7/2016 | Mate et al. | |
| 2017/0367729 A1 * | 12/2017 | Ginggen | A61B 17/205 |
| 2019/0091113 A1 * | 3/2019 | Danto | A61K 8/0204 |

\* cited by examiner

SMOKE EVACUATION SYSTEM

TECHNOLOGY FIELD

Air evacuation system for removal of aerosolized chemical compounds and biological fine particles produced during laser treatment of tissue.

BACKGROUND

The laser devices that are used for skin treatment and in particular for hair removal, pigmented spots removal, skin ablation and other skin treatment procedures performed by application of localized extreme heat cause plumes of smoke to arise as intense heat is applied to flesh. It has been shown that this smoke, also known as laser plume in laser applications and diathermy smoke in electrocautery applications, contains compounds that are potentially harmful to the health of the personnel participating in the operation. The smoke plume also contains ultrafine particulate by-products, particles that are less than 1μ (micron) in diameter, which are undesirable because of the odor, the ability to bypass natural filters and reach the deep alveolar space, and their potential carcinogenic properties.

Current approach to eliminate these by-products and the unpleasant odor caused by the laser plume is the use of so-called smoke extraction devices. Such devices usually include a pump, an external high efficiency particulate air (HEPA) filter attached to a hose, which is held in proximity to the area of laser beam operation. The devices operate continuously and require evacuation of high volumes of air. Use of such devices is sub-optimal owing to the need of either a second operator to hold and maneuver the filter hose or the primary operator to maneuver both the laser delivery device and evacuator hose, and the inconvenience of the large diameter hose that frequently needs to be applied to a small skin area. Evacuation of high volumes of air requires use of large and noisy vacuum pumps which need to be run continuously to generate the high air flow rates required for effective removal of the undesirable by-products.

The following US Patents and Patent Application Publications describe different apparatuses and methods of smoke extractions U.S. Pat. Nos. 5,336,218, 5,575,789, 5,768,740, 5,908,403, 8,641,488, 2016/0193635 and Patent Cooperation Treaty Publications WO1997/014364A1, WO1998/004200A1.

SUMMARY

List of Drawings and their Brief Description

DESCRIPTION

This current disclosure suggests resolving the smoke and particulate by-products problem by integrating a pulsed smoke evacuator and filtration elements into one or more of elements of a skin treatment system. In some examples, more than one smoke filtration elements could be incorporated into the system. The pulsed smoke evacuation could be achieved by coupling a low capacity vacuum pump to a vacuum valve and a reservoir to create very high flow rate for very short durations. The air flow could begin prior to the application of a laser energy pulse to the skin, concurrently with the application of the laser energy pulse and continue after the application of the laser energy pulse. The high flow rates occur at a relatively low duty cycle by opening/closing of the vacuum valve and use of reduced air pressure in the reservoir. Operation of the vacuum valve is synchronized with the treatment laser and in particular with the laser trigger. Before being exhausted from the vacuum pump, the evacuated smoke and particulate by-products could be passed through a liquid, which could be a solvent or a combination of solvents that would facilitate almost complete extraction of the smoke and undesirable laser skin treatment by-products, including small noxious gas molecules and aerosolized organic compounds. Specific compounds such as dimethyl sulfide and trimethyl sulfate have been previously reported by Chuang et al. (JAMA Dermatology 2016; 152(12): 1320-1326) which is included here in total as reference. The smoke could be passed through one or more particle filters to remove larger particulates in the smoke, and/or subsequently could be passed through a liquid which will dissolve harmful chemical constituents of the smoke.

Laser trigger can include the release of a cryogen spray cooling skin prior to the firing of the laser and may even include a post laser cryogen spray for additional skin cooling. Operation of the vacuum valve is synchronized to open after the delivery of the cryogen spray but prior to or subsequent with the firing of the treatment laser. In addition vacuum valve is synchronized to close prior to the start of the post-laser cryogen spray.

Figure 1:
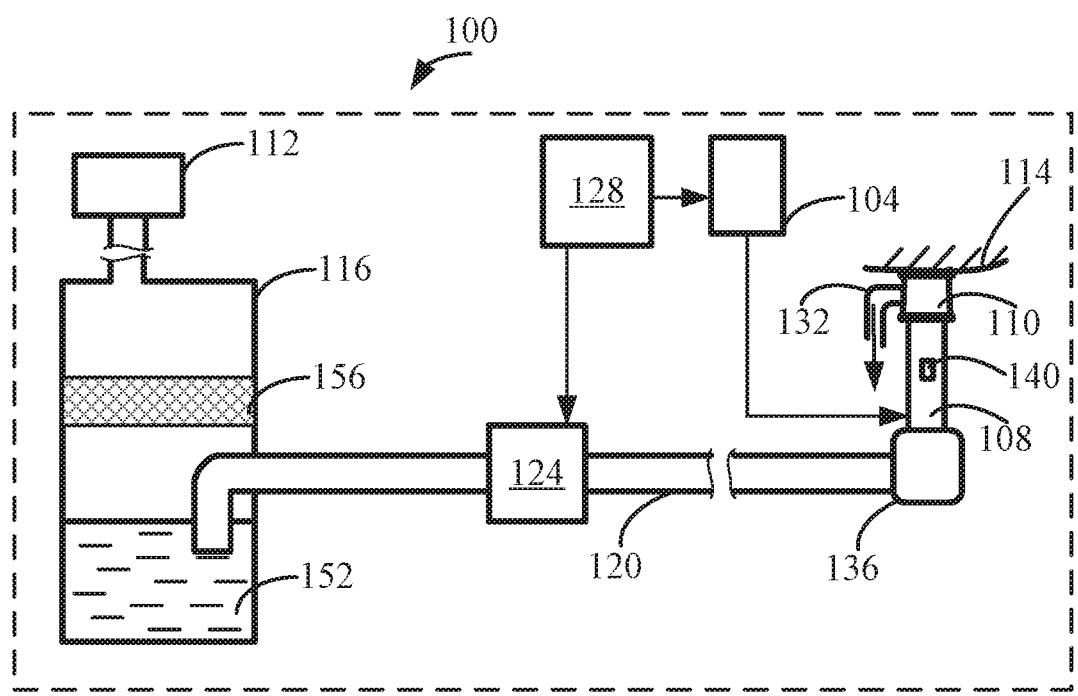
FIG. 1 is a schematic illustration of a smoke evacuation or extraction system according to an example.

FIG. 1 is a schematic illustration of a smoke evacuation or extraction system according to an example. System 100 includes a laser 104 and a laser handpiece 108. Laser handpiece 108 is terminated by a sleeve 110 configurable for application to a patient skin 114. Laser handpiece 108 is receiving laser energy from laser 104. The smoke evacuation or extraction system also includes a vacuum pump 112 and a reservoir 116 containing air at a reduced (negative) pressure. Reservoir 116 through a conduit 120 is in fluid communication with a smoke filter 136 shown associated with laser handpiece 108. In order to reduce noise in the treatment room, vacuum pump 112 could be located remote from laser handpiece 108.

A high speed electrically controlled valve 124 is inserted into conduit 120 and is operative to open and close the fluid communication between sleeve 110 and vacuum reservoir 116. System 100 further includes a processor 128. Processor 128 controls and synchronizes operation of system 100 and in particular the operation of high speed electrically controlled valve 124 and the operation of laser 104.

Smoke filter 136 could be a HEPA filter commonly found in clean rooms and air conditioning systems designed to filter particulates. Smoke filter 136 could include carbon activated air filters for removing volatile organic compounds and odors. Pellets, flocked honeycomb, V-shaped cells of flocked honeycomb, and bonded flocked carbon panels are examples of carbon activated air filters. Smoke filter 136 could be a liquid-phased filter 152 such as water for removing very fine particulates. U.S. Pat. No. 5,908,493 is given here as reference. Other liquids based on their solubility could be used as the filtering material to reduce specific components that are soluble in the liquid. Specific malodor components can include hydrogen sulfide, dimethyl sulfide, and trimethyl sulfate. Smoke filter 136 could be a combination of two or more of a particulate filter, activated carbon filter, or liquid filter.

Figure 1A:
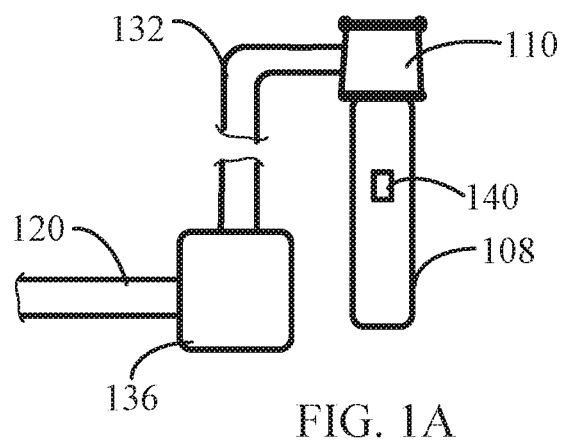
FIG. 1A is a schematic illustration of a smoke evacuation or extraction system similar to FIG. 1 but with a smoke filter located in conduit.

Smoke filter 136 of smoke evacuation or extraction system 100 is configured to filter smoke and particulate by-products generated by skin treatment procedures. In one example smoke filter 136 (FIG. 1) is integrated with laser handpiece 108. In another example smoke filter 136 could be located in conduit 120 (FIG. 1A) or vacuum reservoir 116. Tubing 132 supporting fluid communication between sleeve 110 and smoke filter 136 could be a flexible tubing facilitating easy operation and translation of laser handpiece 108. Tubing 132 supporting fluid communication between sleeve 110 and smoke filter 136 could be positioned internally or externally relative to the shell of the handpiece. Tubing 132 supporting fluid communication between sleeve 110 and smoke filter 136 could be integrated as a hollow chamber within the shell of the handpiece.

Smoke filter 136 could be integrated with a particle filter 156 located in reservoir 116. Smoke filter 136 could be a replaceable and disposable filter. Smoke filter 136 could also be integrated into sleeve 110 and both smoke filter 136 and sleeve 110 could be replaceable and disposable. Smoke filter 136 can also be designed to prevent or reduce loss of fluid 152 via air evacuation through the reservoir 116. Reservoir 116 containing one or more of particle filter 136 and solvent 152 could be designed to be replaceable and disposable. For example fluid 152, such as a solvent could also serve as a smoke filter. In one example, a complete air (vacuum) reservoir 116 including smoke and particle filter 156 could be implemented as a user replaceable and disposable element. Such combined vacuum reservoir and smoke filter, represent a single part/element that serves the function of holding a negative (reduced) air pressure (vacuum) as well as filtering odors, viruses, and other particulates from the air that is drawn in reservoir 116 due to the vacuum.

A system activation switch 140 incorporated into handpiece 108 activates laser 104 and smoke evacuation or extraction system 100. In some examples, system 100 activation switch could be a footswitch. Generally, system 100 activation switch could be associated with any unit/element of system 100.

Figure 2A:
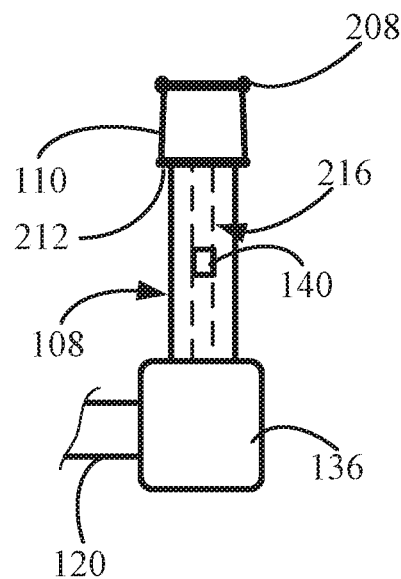
FIGS. 2A and 2B are schematic illustrations of a sleeve of a smoke evacuation system according to an example.
Figure 2B:
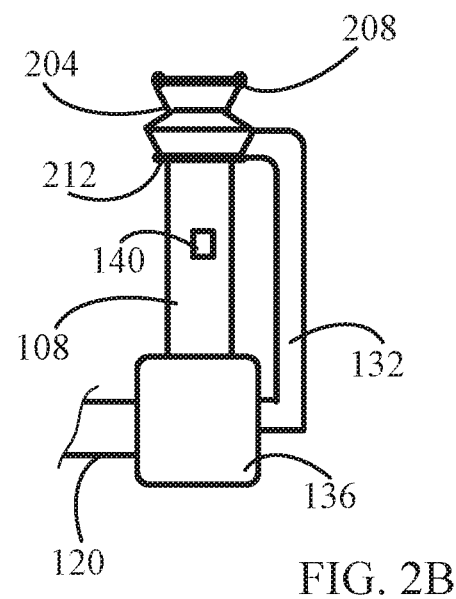

FIGS. 2A and 2B are schematic illustrations of a sleeve of a laser handpiece of a smoke evacuation system according to an example. As shown above, sleeve 110 is associated with laser handpiece 108. In one example, sleeve 110 could be a disposable rigid sleeve made of a biologically compatible plastic material (FIG. 2A). In another example, sleeve 204 could be a flexible sleeve, for example a bellow (FIG. 2B). In both cases the sleeve (110 and 204) may be terminated by a type of gasket or O-ring 208 that could be made of silicone or material similar to the sleeve material. Gasket or O-ring 208 supports air tight application of laser handpiece 108 on any surface and in particular on the surface of the skin. The opposite end of sleeve 110 or 204 is also terminated by a gasket or O-ring 212 forming an air tight connection with laser handpiece 108. When applied to skin 114 (FIG. 1) the sleeve forms a confined/vacant volume. For typical laser skin treatments, the confined/vacant volume could be cylindric in shape having a diameter of 2 inches and a length of 2 inches, roughly 0.1 cubic decimeter. Small volumes can also be envisioned such as a 1 inch diameter and a 1 inch length or roughly 0.01 cubic decimeter. Other shapes besides cylindrical with similar volumes are envisioned. Sleeve 110 and 204 could be used without a gasket or O-ring 208 including allowing laser skin treatment while hovering close to the treatment surface but without touching the skin surface.

Whether using sleeve 110 or 204 with or without a gasket 208, sleeve 110 or 204 may include well placed inlets to allow an inflow of air during the pulsed evacuation procedure. The cross-section of the one or more inlets is designed to be big enough so as to not impede air flow. The inlets could be one or more cut channels placed at the distal end of sleeve 110 or 204. The inlets may be more complex and placed in a specific pattern and may be finned so as to allow a vortex of air flow within the confined/vacant volume moving contaminated air away from central portion axial to the laser beam. U.S. Pat. No. 5,768,740 is incorporated by reference in its entirety herein.

The vacant volume of sleeves 110 or 204 is small and the smoke and particulate by-products generated by the skin treatment procedures could be easy evacuated by a low capacity flow rates in the range of 0.5 to 1000 lpm, or flow rate between 0.5 and 100 lpm, or more specifically 0.5 to 50 lpm.

Sleeve 110 or 204 including gaskets 208 and 212 could be a disposable sleeve. Such sleeve could be disposed after each use. Accordingly, sleeve 110 or 204 could be made as an easy removable and exchangeable sleeve.

In one example (FIG. 2A), handpiece 108 includes a channel 216 conducting smoke and particulate by-products from sleeve 110 or 204 to a smoke filter 136. In another example, the smoke and particulate by-products could be conducted from sleeve 110 or 204 to a smoke filter by relative to the handpiece shell an external or internal tubing 132.

To support rapid evacuation of the smoke and particulate by-products generated by the skin treatment procedures and still use a small vacuum pump 112, pump 112 evacuates air from vacuum reservoir 116 and maintains low level or reduced pressure in reservoir 116. The volume of vacuum reservoir 116 is made at least 2 times larger than the air volume confined in the sleeve. In some examples the volume of vacuum reservoir is made at least 20 times or even 100 times larger than the volume of sleeves 110 or 204.

When high speed electrically controlled valve 124 opens the small volume of sleeves 110 and/or 204, containing smoke and particulate products or particles generated by the skin treatment procedures treatment is almost instantly evacuated into reservoir 116 and from there is further evacuated by vacuum pump 112. Accordingly, the combination of a large vacuum reservoir and a low capacity vacuum pump 112 could still provide high instantaneous flow rates sufficient for evacuation of skin treatment smoke and by products.

Figure 3A:
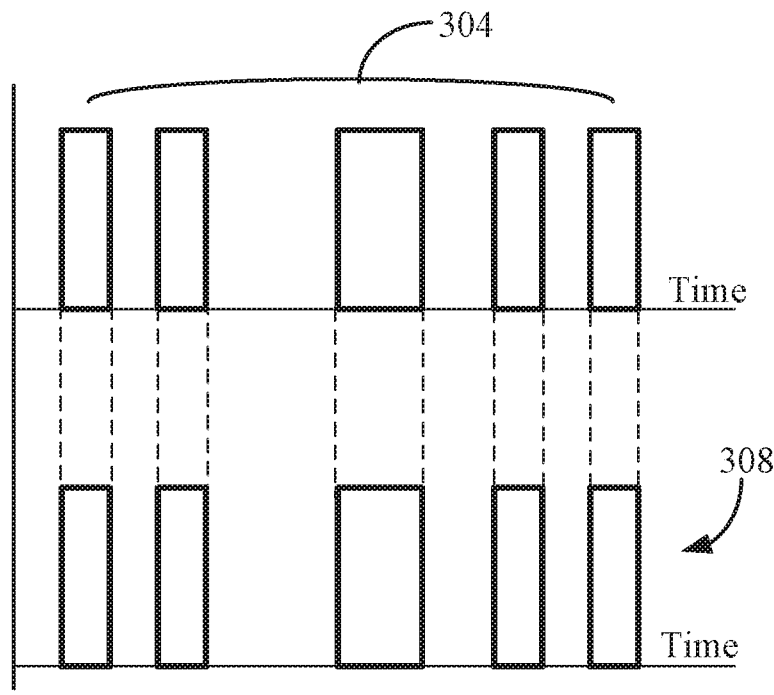
FIGS. 3A and 3B are timing diagrams illustrating synchronous operation of some of the system of FIG. 1 elements.
Figure 3B:
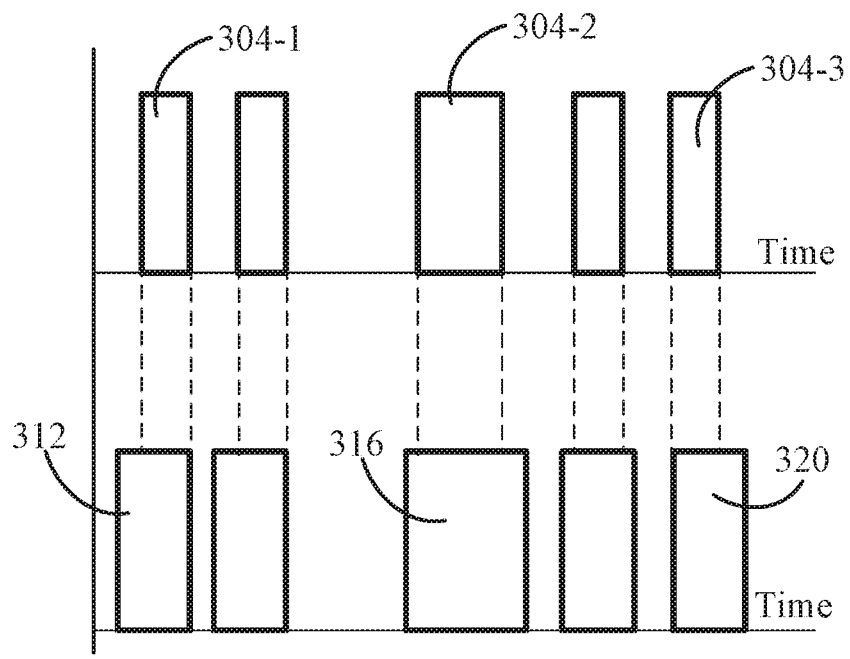

FIGS. 3A and 3B are timing diagrams illustrating synchronous operation of some of the system of FIG. 1 elements. In one example (FIG. 3A) processor 128 synchronizes operation of system 100 such that high speed electrically controlled valve 124 opens and closes communication between sleeve 110 (204) and reservoir 116, as shown by open/close pulses 308, synchronously with the operation of laser 104 emitting laser energy pulses 304. High speed electrically controlled valve 124 also could open communication between sleeve 110 (204) and reservoir 116 just prior to the start of the laser pulse and close communication between the sleeve and the reservoir just after the end of the laser pulse.

In another example (FIG. 3B) operation of high speed electrically controlled valve 124 opens and closes asynchronously with the operation of laser 104 emitting laser energy pulses 304. High speed electrically controlled valve 124 could open 312 before laser pulse 304-1 and close with the termination of laser pulse 304-1; valve 124 could open 316 before laser pulse 304-2, continue during the length of the pulse and close some time after the termination of laser pulse 304-2; valve 124 could open 320 synchronous with laser pulse 304-3, continue the length of the pulse and close some time after the termination of laser pulse 304-3.

The laser pulse duration depends on a particular skin treatment procedure that the caregiver performs and could vary from 1 microsecond to 100 millisecond or more. Some skin treatment procedures are performed by a scanning laser beam. Although the laser beam is scanned along the treated skin segment, the laser energy is typically delivered to the skin in pulse mode. The smoke evacuation system described above and method for smoke evacuation is also applicable to such quasi-continuous laser operation.

The smoke and particles generated by the skin treatment procedures evacuation system can be combined with different ablative and non-ablative laser skin treatment products. The smoke and particulate by-products system reduces the cost of the equipment and noise produced by the vacuum pumps and improves skin treatment procedures environment.

What is claimed is:

1. A rapid pulsatile smoke extraction system comprising:
a laser handpiece terminated by a sleeve configurable for application to a patient skin;
a laser providing laser energy to the laser handpiece;
a reservoir containing air at vacuum pressure, the reservoir is in fluid communication with the sleeve;
a valve configured to open and close communication between the sleeve and the reservoir; and
a processor configurable to control operation of at least the valve,
wherein operation of the valve is synchronized with the operation of the laser, and
wherein the valve opens communication between the sleeve and the reservoir just prior to start of a laser pulse and closes communication between the sleeve and the reservoir just after end of a laser pulse.

2. The system of claim 1 wherein the sleeve is a removable sleeve and a disposable sleeve.

3. The system of claim 1 wherein the sleeve when applied to skin forms a volume in communication with the reservoir for evacuation of the smoke.

4. The system of claim 1 wherein the sleeve is one of a group of sleeves consisting of a rigid sleeve and a flexible sleeve.

5. The system of claim 1 further including a vacuum pump configured to generate the vacuum pressure in at least the reservoir.

6. The system of claim 5 wherein the vacuum pump has a flow capacity of 0.5 liters per minute to 1000 liters per minute.

7. The system of claim 5 wherein the vacuum pump has a flow capacity 0.5 liters per minute to 50 liters per minute.

8. The system of claim 1 further comprising a smoke filter configured to filter smoke and particles generated by skin treatment procedures.

9. The system of claim 8 wherein the smoke filter is at least one of a group of filters consisting of a filter integrated with laser handpiece, integrated into a reservoir, integrated into a conduit conducting smoke from a sleeve to a reservoir, and integrated directly into the sleeve.

10. The system of claim 8, wherein the smoke filter is integrated directly into the sleeve.

11. The system of claim 10, wherein the reservoir includes a smoke and particulate by-products filter, the reservoir connected by a tubing to a vacuum pump.

12. The system of claim 11, wherein the smoke and particulate by-products filter includes a fluid and wherein the fluid is a solvent.

13. The system of claim 1 wherein volume of the reservoir containing air at a reduced pressure is at least twice larger than the volume of the sleeve.

14. The system of claim 1 wherein the system includes an activation switch.

15. The system of claim 1 wherein the handpiece includes a channel conducting smoke from the sleeve to at least a smoke filter.

16. A rapid pulsatile smoke extraction smoke evacuation system for skin treatment, comprising:
a laser handpiece and a laser providing laser energy to the handpiece;
a vacuum reservoir and a valve connecting between the vacuum reservoir and the laser handpiece; and
a processor configured to synchronize operation of the laser and the valve such that each valve opening is synchronized with a laser pulse emitted by the laser.

* * * * *